(12) United States Patent
Brinkman

(10) Patent No.: US 9,534,029 B2
(45) Date of Patent: Jan. 3, 2017

(54) METHOD OF PURIFYING PROTEINS

(71) Applicant: CSL Behring AG, Bern (CH)

(72) Inventor: Nathan Brinkman, Herscher, IL (US)

(73) Assignee: CSL Behring AG, Bern (CH)

( * ) Notice: Subject to any disclaimer, the term of this patent is extended or adjusted under 35 U.S.C. 154(b) by 354 days.

(21) Appl. No.: 13/803,525

(22) Filed: Mar. 14, 2013

(65) Prior Publication Data

US 2014/0094411 A1 Apr. 3, 2014

Related U.S. Application Data

(60) Provisional application No. 61/709,342, filed on Oct. 3, 2012.

(51) Int. Cl.
- C07K 14/00 (2006.01)
- C07K 14/435 (2006.01)
- C07K 14/47 (2006.01)
- C07K 14/79 (2006.01)

(52) U.S. Cl.
CPC ........... *C07K 14/4717* (2013.01); *C07K 14/47* (2013.01)

(58) Field of Classification Search
None
See application file for complete search history.

(56) References Cited

U.S. PATENT DOCUMENTS

| | | | |
|---|---|---|---|
| 2,390,074 A | 12/1945 | Cohn | |
| 2,469,193 A | 5/1949 | Cohn | |
| 4,061,735 A * | 12/1977 | Funakoshi et al. | 514/3.7 |
| 4,103,687 A | 8/1978 | Ishii | |
| 4,129,648 A * | 12/1978 | Collier et al. | 530/392 |
| 4,540,573 A | 9/1985 | Neurath et al. | |
| 4,704,274 A | 11/1987 | Sakuma et al. | |
| 4,764,369 A | 8/1988 | Neurath et al. | |
| 4,841,026 A | 6/1989 | Van Beveren et al. | |
| 5,041,537 A | 8/1991 | Bethke et al. | |
| 5,138,034 A | 8/1992 | Uemura et al. | |
| 5,169,936 A | 12/1992 | Staples et al. | |
| 5,252,715 A | 10/1993 | Haupt | |
| 5,744,586 A | 4/1998 | Rolf et al. | |
| 6,093,804 A * | 7/2000 | Ralston et al. | 530/416 |
| 6,251,860 B1 | 6/2001 | Parkkinen et al. | |
| 7,041,798 B1 | 5/2006 | Kothe et al. | |
| 7,285,646 B2 | 10/2007 | Bauer | |
| 7,795,010 B2 | 9/2010 | Tanahashi et al. | |
| 7,919,592 B2 | 4/2011 | Lengsfeld et al. | |
| 2005/0153875 A1* | 7/2005 | Bauer | 514/6 |
| 2005/0220788 A1 | 10/2005 | Nagy et al. | |
| 2006/0140966 A1 | 6/2006 | Srivastava | |
| 2006/0228328 A1 | 10/2006 | Srivastava | |
| 2008/0096233 A1 | 4/2008 | Robotti et al. | |
| 2008/0176254 A1 | 7/2008 | Fang et al. | |
| 2008/0293623 A1 | 11/2008 | Dalton et al. | |
| 2009/0175797 A1 | 7/2009 | Warren et al. | |
| 2009/0281282 A1* | 11/2009 | Dalton et al. | 530/364 |
| 2011/0021418 A1* | 1/2011 | Dalton | A61K 38/1709 514/4.4 |
| 2011/0294988 A1 | 12/2011 | Blackwell et al. | |
| 2012/0122179 A1 | 5/2012 | Perret et al. | |

FOREIGN PATENT DOCUMENTS

| | | |
|---|---|---|
| AU | 1988 27132 A | 6/1989 |
| AU | 1988 27132 A | 6/1989 |
| GB | 1426039 | 2/1976 |
| JP | 62036494 B4 | 8/1987 |
| JP | 63017899 A2 | 1/1988 |
| JP | 9077680 A2 | 3/1997 |
| JP | 2003096095 A2 | 4/2003 |
| JP | 3560066 B2 | 9/2004 |
| JP | 2004244348 A2 | 9/2004 |
| JP | 3825061 B2 | 9/2006 |
| WO | WO 89/04965 | 6/1989 |
| WO | WO 99/20787 | 4/1999 |
| WO | WO 2006/018428 A2 | 2/2006 |
| WO | WO 2006/043062 | 4/2006 |
| WO | WO 2008/088403 A2 | 7/2008 |
| WO | WO 2009/025754 | 2/2009 |
| WO | WO 2011/060438 A2 | 5/2011 |
| WO | WO 2011/098990 A1 | 8/2011 |

OTHER PUBLICATIONS

Sun et al., Artif Cells Blood Substit Immobil Biotechnol (2011) 39, 79-86.*

Durán et al., Arthritis Rheum. (2009) author manuscript available in PMC, http://www.ncbi.nlm.nih.gov/pmc/articles/PMC2760833/pdf/nihms-130623.pdf).*

Extended European Search Report dated Oct. 2, 2013, for European Patent Application 13 170 202.9 (11 pages).

Baek, J.H. et al.; "Hemoglobin-driven pathophysiology is an in vivo consequence of the red blood cell storage lesion that can be attenuated in guinea pigs by haptoglobin therapy," The Journal of Clinical Investigation; Apr. 2012; vol. 122, No. 4; pp. 1444-1458.

Bernard, N. et al.; "Isolement et propriétés physic-chimiques de l'hémopexine de rat (Isolation and physical chemical properties of rat hemopexin)," Biochimie; 1975; vol. 57, No. 5; pp. 551-557.

Cox, A.M. et al.; "Separation and characterisation of glycoproteins from normal, pregnancy, and acute inflammatory sera," Journal of Chromatography; 1987; vol. 397; pp. 213-222.

Mauk, M. R. et al.; "Metal Ion Binding to Human Hemopexin," Biochemistry; 2005; vol. 44, No. 6; pp. 1864-1871.

Mauk, M.R. et al.; "An alternative view of the proposed alternative activities of hemopexin," Protein Science; May, 2011; vol. 20; pp. 791-805.

Parra, M.D. et al.; "Development of a time-resolved fluorometry based immunoassay for the determination of canine haptoglobin in various body fluids," Vet. Res.; 2005; vol. 36; pp. 117-129.

Takahashi, N. et al.; "Purification of hemopexin and its domain fragments by affinity chromatography and high-performance liquid chromatography," Journal of Chromatography; 1985; vol. 326; pp. 373-385.

(Continued)

*Primary Examiner* — Karlheinz R Skowronek
*Assistant Examiner* — Catherine Mader
(74) *Attorney, Agent, or Firm* — Finnegan, Henderson, Farabow, Garrett & Dunner, LLP

(57) ABSTRACT

The present invention relates generally to a method of purifying proteins. More specifically, the present inventions relates to a method of purifying haptoglobin and hemopexin from the same starting material, and uses thereof.

12 Claims, 10 Drawing Sheets

(56) References Cited

OTHER PUBLICATIONS

International Search Report and Written Opinion dated Oct. 1, 2013, for PCT/US2013/062916 (19 pages).
Ascione, Ester. et al.; "A simple method for large-scale purification of plasma-derived apo-transferrin," *Biotech.Appl. Biochm.*; (2010); vol. 57, pp. 87-95.
Koechlin, "Preparation and Properties of Serum and Plasma Proteins. XXVIII. The $\beta_1$-Metal-combining Protein of Human Plasma," May 20, 1952, 2649, The University Laboratory of Physical Chemistry Related to Medicine and Public Health, Harvard University.
Kistler et al., "Humanes Siderophilin: Isolierung mittels Rivanol aus Blutplasma und Plasmafraktionen, analytische Bestimmung und Kristallisation," Vox Sang. 5:403-415 (1960), Zentrallaboratorium des Blutspendedienstes des Schweizerischen Roten Kreuzes und Theodor-Kocher-Institut der Universität Bern.
Inman et al., "A Large-Scale Method for the Purification of Human Transferrin," Vox Sang. 6:34-52 (1961), Division of Laboratories, Michigan Department of Health, Lansing, Mich.
Kalous et al., "Haptoglobin Properties of a Serum M-2 Component," Archives of Biochemistry and Biophysics 106, 489-497 (1964), Department of Physical Chemistry, Charles University, Prague, Czechoslovakia.
Oh et al., "Chromatographic Subfractionation and Characterization of Cohn's Fraction III from Human Plasma," Analytical Biochemistry 16, 220-224 (1966), Department of Biochemistry, School of Medicine, State University of New York at Buffalo, Buffalo, New York.
Hamaguchi et al., "Control of Haptoglobin Metabolism. III Purification of the Hemoglobin-Haptoglobin 'Subunit' and the Hemoglobin-Haptoglobin Complex from Human Serum of the Haptoglobin 1-1 Type," Proc. Japan Acad., 43 (1967), p. 332, Department of Clinical Genetics, Tokyo Medical and Dental University, Tokyo.
Betlach et al., "Purification of Haptoglobin and α2-Macroglobulin from Human Serum," Analytical Biochemistry 49, 103-108 (1972), Academic Press, Inc.
Aisen et al., "Human Hemopexin Preparation and Magnetic Properties," The Journal of Biological Chemistry, vol. 249, No. 21, Issue of Nov. 10, pp. 6824-6827, 1974.
Saeed et al., "Human haptoglobin: an endogenous inhibitor of prostaglandin synthase," D. A. Willoughby et al. (eds.), p. 285, *Inflammation: Mechanisms and Treatment*, MPT Press Limited 1980.
Barnes et al., "Separation of Albumin, Ceruloplasmin, and Transferrin from Human Plasma," Oct. 1982, p. 873-874, Journal of Chemical Education, vol. 59, No. 10, Florida State University, Tallahassee, FL 32306.
Tsutsui et al., "Affinity Chromatography of Heme-Binding Proteins: An Improved Method for the Synthesis of Hemin-Agarose," Analytical Biochemistry 121, 244-250, Academic Press, Inc., (1982).
Strahler et al., "Separation of Transferrin Types in Human Plasma by An-Ion-Exchange High-Performance Liquid Chromatography," Journal of Chromatography, 266 (1983) 281-291, Elsevier Science Publishers B.V.
Werner et al., "Communication DEAE-Affi-Gel Blue Chromatography of Human Serum: Use for Purification of Native Transferrin," Archives of Biochemistry and Biophysics, vol. 226, No. 1, Oct. 1, pp. 393-398, 1983, Academic Press Inc.
Andersson "Fractionation of Human Serum Proteins by Immobilized Metal Affinity Chromatography," Journal of Chromatography, 315 (1984) 167-174, Elsevier Science Publishers B.V., Amsterdam.
Chung et al., "Studies on Equine Transferrin-I. The Isolation and Partial Characterization of the D and R Variants," Comp. Biochem. Physiol. vol. 80B, No. 2, pp. 287-297, 1985, Pergamon Press Ltd, Great Britain.
Cook et al., "Rapid Preparation of Highly Purified Human Transferrin," Analytical Biochemistry 149, 349-353 (1985), Academic Press, Inc.
Birkenmeier et al., "Fractionation of proteins from human serum by counter-current distribution," Journal of Biotechnology, 5 (1987) 115-129, Elsevier Science Publishers B.V. (Biomedical Division).
Welch et al., "A Comparison of the Structure and Properties of Human, Rat and Rabbit Serum Transferrin," Comp. Biochem. Physiol. vol. 93B, No. 2, pp. 417-424, 1989, Pergamon Press plc.
Jensen et al., "Zinc Chelates Bind Human Hemopexin," Acta Chemica Scandinavica (1991) 45: 537-538.
Rivat et al., "Single-step method for purification of human transferrin from a by-product of chromatographic fractionation of plasma," Journal of Chromatography, 576 (1992) 71-77, Biomedical Applications, Elsevier Science Publishers B.V., Amsterdam.
Van Gelder et al., "Isolation, purification and characterization of porcine serum transferrin and hemopexin," Comp. Biochem. Physiol. vol. 111B, No. 2, pp. 171-179, 1995, Elsevier Science Ltd, Great Britain.
Von Bonsdorff et al., "Development of a Pharmaceutical Apotransferrin Product for Iron Binding Therapy," Biologicals (2001) 29, 27-37, doi:10.1006/biol.2001.0273, available online at http://www.idealibrary.com, The International Association for Biologicals.
Arefanian et al., "A New Protocol for Isolation and Purification of Transferrin from Human Serum," Iranian J. Publ. Health, vol. 31, Nos. 1-2, pp. 15-18, 2002, downloaded from http://journals.tums.ac.ir/.
Tseng et al., "Purification of human haptoglobin 1-1, 2-1, and 2-2 using monoclonal antibody affinity chromatography," Protein Expression and Purification 33 (2004) 265-273, Elsevier Inc.
McCann et al., "Purification of transferrin from Cohn supernatant I using ion-exchange chromatography," Biotechnol. Appl. Biochem. (2005) 42, 211-217, doi:10.1042/BA20050065, Portland Press Ltd, Great Britain.
Kumpalume et al., "Designing a new manufacturing processes for plasma proteins to maximise alpha-1 antitrypsin recovery," Food and Bioproducts Processing 86 (2008) 65-73, Elsevier B.V. on behalf of The Institution of Chemical Engineers, doi:10.1016/j.fbp.2007.10.006.
Fuentes et al., "Development of Fast and Simple Methods for Porcine Haptoglobin and Ceruloplasmin Purification," An. Vet. (Murcia) 26:43-54(2010).
Kong et al., "An automatic system for multidimensional integrated protein chromatography," Journal of Chromatography A, 1217 (2010) 6898-6904, Elsevier B.V., doi:10.1016/j.chroma.2010.08.067.
Sun et al., "A Simple and Rapid Procedure for Purification of Haptoglobin from Human Plasma Fraction IV," Artificial Cells, Blood Substitutes, and Biotechnology, 39:79-86, 2011, Informa Healthcare USA, Inc., DOI: 10.3109/10731199.2010.509705.
Anderson et al., "Structure of the haptoglobin-haemoglobin complex," 456 Nature Vo. 489, Sep. 20, 2012, Macmillan Publishers Limited, doi:10.1038/nature11369.

\* cited by examiner

10% Tris-Glycine SDS-PAGE of Capto-Q Load and Column Fractions

METHOD OF PURIFYING PROTEINS

CROSS REFERENCE

This application claims the benefit of U.S. Provisional Patent Application No. 61/709,342, filed Oct. 3, 2012, which is hereby incorporated by reference.

TECHNICAL FIELD

The present invention relates generally to a method of purifying proteins. More specifically, the present inventions relates to a method of purifying haptoglobin and hemopexin from the same starting material, and uses thereof.

BACKGROUND

Haemolysis is characterized by the destruction of red blood cells and is a hall-mark of anaemic disorders associated with red blood cell abnormalities, such as enzyme defects, haemoglobinopathies, hereditary spherocytosis, paroxysmal nocturnal haemoglobinuria and spur cell anaemia, as well as extrinsic factors such as splenomegaly, autoimmune disorders (e.g., Hemolytic disease of the newborn), genetic disorders (e.g., Sickle-cell disease or G6PD deficiency), microangiopathic haemolysis, Gram-positive bacterial infection (e.g., *Streptococcus, Enterococcus* and *Staphylococcus*), parasite infection (e.g., *Plasmodium*), toxins and trauma (e.g., burns). Haemolysis is also a common disorder of blood transfusions, particularly massive blood transfusions and in patients using an extracorporeal cardiopulmonary support.

The adverse effects seen in patients with conditions associated with haemolysis are largely attributed to the release of iron and iron-containing compounds, such as haemoglobin (Hb) and heme, from red blood cells. Under physiological conditions, released haemoglobin is bound by soluble proteins such as haptoglobin and transported to macrophages and hepatocytes. However, where the incidence of haemolysis is accelerated and becomes pathological in nature, the buffering capacity of haptoglobin is overwhelmed. As a result, haemoglobin is quickly oxidised to ferri-haemoglobin, which in turn releases free heme (comprising protoporphyrin IX and iron). Whilst heme plays a critical role in several biological processes (e.g., as part of essential proteins such as haemoglobin and myoglobin), free heme is highly toxic. Free heme is a source of redox-active iron, which produces highly toxic reactive oxygen species (ROS) that damages lipid membranes, proteins and nucleic acids. Heme toxicity is further exacerbated by its ability to intercalate into lipid membranes, where is causes oxidation of membrane components and promotes cell lysis and death.

The evolutionary pressure of continuous low-level extracellular Hb/heme exposure has led to compensatory mechanisms that control the adverse effects of free Hb/heme under physiological steady-state conditions and during mild haemolysis. These systems include the release of a group of plasma proteins that bind Hb or heme, including the Hb scavenger haptoglobin (Hp) and the heme scavenger proteins hemopexin (Hx) and α1-microglobulin. However, whilst endogenous Hp and Hx control the adverse effects of free Hb/heme under physiological steady-state conditions, they have little effect in maintaining steady-state Hb/heme levels under pathophysiogical conditions, such as those associated with haemolysis.

The present invention provides a method of purifying Hp and Hx from the same starting material. The purified proteins can be used in compositions for treating conditions associated with haemolysis and aberrant Hb/heme levels.

SUMMARY OF THE INVENTION

In an aspect of the present invention, there is provided a method of purifying haptoglobin and hemopexin from a solution containing both proteins, the method comprising:
  (i) providing a solution containing both haptoglobin and hemopexin;
  (ii) precipitating the haptoglobin from the solution by adding ammonium sulphate to the solution;
  (iii) separating the precipitated haptoglobin from the solution containing hemopexin; and
  (iv) separately purifying the haptoglobin and/or hemopexin in one or more steps.

In another aspect of the present invention, there is provided a composition comprising the haptoglobin recovered by the methods disclosed herein.

In another aspect of the present invention, there is provided a composition comprising the hemopexin recovered by the methods disclosed herein.

In another aspect of the present invention, there is provided a composition comprising the transferrin recovered by the methods disclosed herein.

In another aspect of the present invention, there is provided a composition comprising the haptoglobin recovered by the methods disclosed herein and the hemopexin recovered by the methods disclosed herein.

In another aspect of the present invention, there is provided a composition comprising a haptoglobin content of at least 80% of total protein. In another aspect of the present invention, there is provided a composition comprising a hemopexin content of at least 80% of total protein. In another aspect of the present invention, there is provided a composition comprising a combined hemopexin and haptoglobin content of at least 80% of total protein.

In another aspect of the present invention, there is provided a formulation comprising the composition of the present invention, as disclosed herein, and a pharmaceutically acceptable carrier.

In another aspect of the present invention, there is provided a method of treating a condition associated with haemolysis, the method comprising administering to a subject in need thereof the composition or the formulation of the present invention, as disclosed herein.

In another aspect of the present invention, there is provided use of the compositions or formulations of the present invention, as disclosed herein, in the manufacture of a medicament for treating a condition associated with haemolysis.

DETAILED DESCRIPTION

Figure 1:
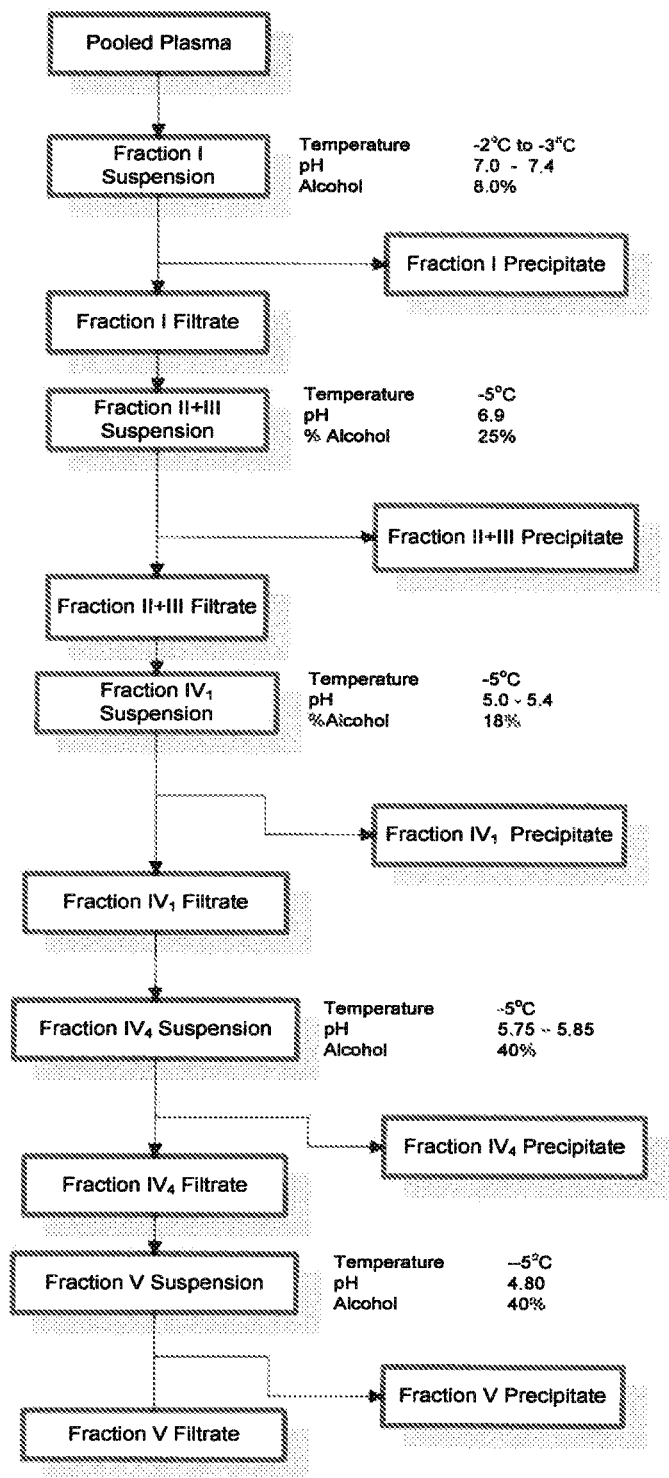
FIG. 1 is a flow diagram of a Cohn Fractionation Process.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It must be noted that, as used in the subject specification, the singular forms "a", "an" and "the" include plural aspects unless the context clearly dictates otherwise. Thus, for example, reference to "a resin" includes a single resin, as well as two or more resins; reference to "the composition" includes a single composition, as well as two or more compositions; and so forth.

In the absence of any indication to the contrary, reference made to a "%" content throughout this specification is to be taken as meaning % w/w (weight/weight). For example, a solution comprising a haptoglobin content of at least 80% of total protein is taken to mean a composition comprising a haptoglobin content of at least 80% w/w of total protein.

The present invention is predicated, at least in part, on the finding that haptoglobin and hemopexin can be purified from the same starting material. Thus, in an aspect of the present invention, there is provided a method of purifying haptoglobin and hemopexin from a solution containing both proteins, the method comprising:
(i) providing a solution containing both haptoglobin and hemopexin;
(ii) precipitating the haptoglobin from the solution by adding ammonium sulphate to the solution;
(iii) separating the precipitated haptoglobin from the solution containing hemopexin; and
(iv) separately purifying the haptoglobin and/or hemopexin in one or more steps.

Haptoglobin (Hp) is a tetrachain ($\alpha_2\beta_2$) glycoprotein synthesized by the adult liver and secreted into the plasma. The propeptide form of Hp is proteolytically cleaved into an $\alpha$-chain and a $\beta$-chain. Two $\alpha$-subunits and two $\beta$-subunits of Hp protein are then joined by inter-chain disulfide bonds to form the mature peptide, which can be either an ($\alpha\beta$)-dimer or an ($\alpha\beta$)-multimer. Hemopexin (Hx) is a 60-kD plasma $\beta$-1B-glycoprotein comprising a single 439 amino acid long peptide chain, which forms two domains joined by an interdomain linker. It has the highest known affinity for heme (Kd<1 pM) of any characterized heme-binding protein and binds heme in an equimolar ratio between the two domains of Hx in a pocket formed by the interdomain linker.

The inventors have found that an ammonium sulfate concentration in the range of about 2.0M to about 2.5M, preferable in the range of about 2.2M to about 2.5M, more preferably about 2.4M, is optimal for separating both proteins from the same starting material. Thus, in an embodiment, the method comprises precipitating the haptoglobin from the solution by adding about 2.0M to about 2.5M ammonium sulphate to the solution. In another embodiment, the method comprises precipitating the haptoglobin from the solution by adding about 2.2M to about 2.5M ammonium sulphate to the solution. In yet another embodiment, the method comprises precipitating the haptoglobin from the solution by adding about 2.4M ammonium sulphate to the solution.

The inventors have also shown that a pH maintained in the range of less than or equal to about 8, preferably about 6 to about 8, more preferably at about 7.0, is optimal for separating both proteins from the same staring material. Thus, in an embodiment, the method comprises precipitating the haptoglobin from the solution at a pH of less than or equal to 8. In another embodiment, the method comprises precipitating the haptoglobin from the solution at a pH within the range of about 6 to about 8. In yet another embodiment, the method comprises precipitating the haptoglobin from the solution at a pH of about 7.

In the methods disclosed herein, the majority of haptoglobin from the starting material will be found within the ammonium sulfate precipitate and the majority of the hemopexin from the starting material will be found in the remaining solution (also referred to as the suspension). However, persons skilled in the art will understand that the precipitate may comprise some hemopexin (e.g., trace amounts of Hx) and that the remaining solution (or suspension) may comprise some haptoglobin (e.g., trace amounts of Hp). Where trace amounts of Hp and Hx are present in the suspension and precipitate, respectively, it may be desirable to remove these by separately purifying the haptoglobin and/or hemopexin in one or more steps in accordance with the methods disclosed herein. However, persons skilled in the art would understand that trace amounts of Hp and Hx that may be present in the suspension and precipitate, respectively, may be acceptable, for example, where both proteins will end up in the same composition.

Any solution comprising both haptoglobin and hemopexin can be used as the staring material in the method of the present invention, disclosed herein. Suitable starting material would be known to persons skilled in the art, examples of which include plasma fractions such as various supernatants and precipitates derived from ethanol fractionation processes. Examples of such ethanol fractionation processes include Cohn fractionation and Kistler-Nitschmann fractionation. Examples of suitable plasma fractions include those derived from a Cohn fraction I, II, III, II+III, I+II+III, IV and V (See FIG. 1) or a Kistler-Nitschmann fraction such as a Precipitate A or B. In an embodiment, the solution is a human plasma fraction. In another embodiment, the solution is a Cohn Fraction IV. In yet another embodiment, the solution is a Cohn Fraction $IV_4$. In a particularly preferred embodiment the solution is derived from a Fraction $IV_4$ Precipitate.

It will be understood that, where the starting material is provided as a precipitate (e.g., Fraction $IV_4$ Precipitate), it will be necessary to initially resolublise the precipitate to provide a suitable starting solution for the methods of the present invention.

The methods of the present invention are suitable for the commercial/industrial scale purification of hemopexin, haptoglobin and, optionally, transferrin. For example, when using plasma fractions as a starting material, employing the method of the present invention on a commercial/industrial scale may involve the use of a plasma fraction derived from at least about 500 kg of plasma. More preferably, the plasma fraction will be derived from at least about 5,000 kg, 7,500 kg, 10,000 kg and/or 15,000 kg of plasma per batch.

The skilled person will understand that plasma for fractionation is the liquid part of blood remaining after separation of the cellular elements from blood collected in a receptacle containing an anticoagulant, or separated by any other suitable means known to persons skilled in the art, such as by continuous filtration or centrifugation of anticoagulated blood in an apheresis procedure.

In an embodiment, the precipitated haptoglobin and the solution containing hemopexin are recovered and stored separately before separately purifying the haptoglobin and/or hemopexin in one or more steps, in accordance with the present invention. In another embodiment, the precipitated haptoglobin and the solution containing hemopexin are recovered and subjected immediately to further purification steps in accordance with the methods of the present invention; that is, separately purifying the haptoglobin and/or hemopexin in one or more steps.

Thus, in an embodiment, the method further comprises:
(i) dissolving the precipitated haptoglobin in a buffer to obtain a haptoglobin solution;
(ii) passing the haptoglobin solution through a strong anion exchange chromatographic resin under conditions such that the haptoglobin binds to the resin;
(iii) eluting the haptoglobin from the resin; and
(iv) recovering the eluted haptoglobin.

Purification of proteins by chromatography can be performed using either axial flow columns, such as those available from GE Healthcare, Pall Corporation and Bio-Rad, or using radial flow columns, such as those available from Proxcys. Chromatography can also be conducted using expanded bed technologies known to persons skilled in the art.

Most chromatographic processes employ a solid support, also referred to interchangeably herein as a resin or matrix. Suitable solid supports would be familiar to persons skilled in the art and the choice will depend on the type of product to be purified. Examples of suitable solid supports include inorganic carriers, such as glass and silica gel, organic, synthetic or naturally occurring carriers, such as agarose, cellulose, dextran, polyamide, polyacrylamides, vinyl copolymers of bifunctional acrylates, and various hydroxylated monomers, and the like. Commercially available carriers are sold under the names of Sephadex™, Sepharose™, Hypercel™, Capto™, Fractogel™, MacroPrep™, Unosphere™, GigaCap™, Trisacryl™, Ultrogel™, Dynospheres™, Macrosorb™ and XAD™ resins.

The chromatography steps will generally be carried out under non-denaturing conditions and at convenient temperatures in the range of about −10° C. to +30° C., more usually at about ambient temperatures. The chromatographic steps may be performed batch-wise or continuously, as convenient. Any convenient method of separation may be employed, such as column, centrifugation, filtration, decanting, or the like.

Buffers that are suitable for dissolving the haptoglobin precipitate would be familiar to persons skilled in the art and may depend on the conditions required for performing the chromatographic purification step. Examples of suitable buffers are sodium acetate and Tris with a pH range of 5.5 to 9.0. Particular embodiments utilize a pH of 7.5 to 9.0 however, in a preferred embodiment the buffer is about 50 mM Tris at a pH of about pH 8.4 to about pH 8.6.

In embodiments the lipid content of the extracted precipitate comprising haptoglobin is reduced by exposure to a lipid removal agent under conditions that allow the lipid to bind to the lipid removal agent. Examples of such agents include fumed silica such as Aerosil. In a preferred embodiment the lipid removal agent is Aerosil. The lipid removal agent such as Aerosil can be added to the extracted precipitate comprising haptoglobin at about 0.5 g to about 4 g per liter of plasma equivalent. In particular embodiments, Aerosil is added at 1 to 2 g per liter plasma equivalent. In a preferred embodiment Aerosil is added at 1.6 g per liter of plasma equivalent. It was determined that lipid removal is most effective within a specific pH range. A pH range of 5.5 to 8.5 was found to be effective in conjunction with Aerosil. The preferred embodiment utilizes a pH range of 8.4 to 8.6.

The lipid removal agent can be removed using methods such as filtration and or centrifugation. In particular embodiments the lipid removal agent is removed by depth filtration. An example of a depth filter for use in this application is a Cuno 70CA filter or one of similar or smaller particle size retention capabilities.

Persons skilled in the art will understand that any strong anion exchange chromatographic resin can be used to separately purify haptoglobin from the haptoglobin solution, as long as the haptoglobin is capable of binding to the chromatographic resin while allowing some impurities in the solution to pass though the resin. Persons skilled in the art would also determine that due to the ionic strength of the extraction buffer and subsequent pH adjustment of the load solution; dilution, diafiltration, or other methods of buffer exchange/ionic strength reduction would be required to allow haptoglobin to bind to the resin. Suitable resins would be known to persons skilled in the art. Examples of suitable anion exchange resins are ones comprising a functional quaternary amine group (Q) and/or a diethylaminopropyl group (ANX). In an embodiment, the strong anion exchange chromatographic resin comprises a functional quaternary amine group (e.g., Capto Q ImpRes™).

Buffers that are suitable for eluting the haptoglobin from the resin will also be known to persons skilled in the art. An example includes sodium acetate. Particular embodiments utilize 50 mM sodium acetate at a pH of 5.0 to 6.0. In a preferred embodiment the buffer is about 50 mM sodium acetate at a pH of about pH 5.3 to about pH 5.7.

In further embodiments, the haptoglobin is eluted from the anion exchange resin with an elution buffer comprising from about 100 mM to about 200 mM NaCl. This equates to an elution buffer having a conductivity range of about 10 mS/cm (100 mM NaCl) to about 18 mS/cm (200 mM NaCl). In particular embodiments the haptoglobin is eluted in the presence of about 150 to 170 mM NaCl. In a preferred embodiment the haptoglobin is eluted in the presence of about 160 mM NaCl.

In an embodiment, the eluted haptoglobin is recovered and stored separately for future use. In another embodiment, the eluted haptoglobin is further purified, for example, by concentrating and diafiltering the eluted haptoglobin through an ultrafiltration membrane and/or sterile filtering the concentrated and/or diafiltering haptoglobin, as required.

In an embodiment, the method further comprises:
(i) passing the solution containing hemopexin through a hydrophobic interaction chromatographic resin under conditions that allow the hemopexin to bind to the resin;
(ii) collecting the flow-through fraction from step (i);
(iii) optionally washing the resin following step (ii) and collecting the flow-through wash fraction; and
(iv) eluting the hemopexin from the resin following step (ii) and/or following step (iii); and
(v) recovering the eluted hemopexin.

Hydrophobic Interaction Chromatography (HIC) is a chromatographic technique frequently used for the separation of proteins on the basis of a hydrophobic interaction between the stationary phase and the protein to be separated. The level of hydrophobicity of the target protein will often dictate the type of HIC resin to be used. During HIC, a high amount of salt is typically added to the solution to reduce the solubility of the target protein and thus increase the interaction of the target protein with the HIC resin functionalized with a suitable hydrophobic groups (e.g., phenyl, butyl and octadecyl groups). Suitable hydrophobic interaction chromatographic resins would be familiar to persons skilled in the art. An example includes an octyl sepharose chromatographic resin. The conditions that allow the hemopexin to bind to the resin will be known to persons skilled in the art and will be dictated, for example, by the type of resin used and the hydrophobicity of the target protein (i.e., hemopexin).

Once the solution containing hemopexin is passed through the hydrophobic interaction chromatographic (HIC) resin, the flow through fraction can be collected and stored for future use, as disclosed herein.

The bound hemopexin can be eluted from the resin by means known to persons skilled in the art. Prior to eluting the hemopexin from the resin, the resin can optionally be washed with a suitable wash solution or buffer under conditions that retain the hemopexin bound to the resin. Suitable wash solutions and conditions will be known to persons skilled in the art. The flow through wash fraction can also be collected and stored for future use, as necessary.

The eluted hemopexin that is recovered from the resin can be stored for future use. The eluted hemopexin may also be subjected to further purification to remove any impurities in the eluate. Thus, in an embodiment, the method further comprises:
(i) passing the eluted hemopexin through a metal ion affinity chromatographic resin under conditions that allow the hemopexin to bind to the resin; and
(ii) eluting the hemopexin from the resin; and
(iii) recovering the eluted hemopexin.

Immobilized metal ion affinity chromatography (IMAC) is based on the covalent attachment of amino acids (e.g., histidine) to metals, allowing proteins with an affinity for metal ions to be retained in a column containing immobilized metal ions, such as zinc, cobalt, nickel or copper. Suitable metal ion affinity chromatographic resins would be known to persons skilled in the art. In an embodiment, the metal ion affinity chromatographic resin is Ni-Sepharose.

Once the hemopexin is bound to the metal ion affinity chromatographic (IMAC) resin, the resin may be washed to remove any residual impurities under conditions that retain the hemopexin bound to the resin. The bound hemopexin can be eluted from the resin by means known to persons skilled in the art. The eluted hemopexin can be further purified, for example, by concentrating and diafiltering the hemopexin through an ultrafiltration membrane and/or sterile filtering the concentrated and/or diafiltering hemopexin, as required.

The inventors have also found that any transferrin that may be present in the starting material remains in solution (i.e., in the solution comprising hemopexin) following the precipitation of haptoglobin in the presence of ammonium sulfate. Thus, the methods of the present invention, disclosed herein, can also be used to purify transferrin from the same starting material. Conditions are therefore provided that are optimal for purifying all three proteins (Hp, Hx and transferrin) from the same starting material. Thus, in an embodiment, the solution containing both haptoglobin and hemopexin (e.g., the starting material) will further comprise transferrin.

In an embodiment, the method further comprises:
(a) passing the solution containing hemopexin through a hydrophobic interaction chromatographic resin under conditions that allow the hemopexin to bind to the resin;
(b) collecting the flow-through fraction from step (a);
(c) optionally washing the resin following step (b) and collecting the flow-through wash fraction;
(d) passing the flow-through fraction from step (b) and/or the flow-through wash fraction from step (c) through a weak anion exchange chromatographic resin under conditions such that transferrin binds to the resin; and
(e) recovering the transferrin from the resin.

Suitable weak anion exchange chromatographic resins will be known to persons skilled in the art. Examples include resins comprising a tertiary or secondary amine functional group, such as DEAE (diethylaminoethyl).

Once the transferrin is recovered from the weak anion exchange chromatographic resin, it can be further purified, for example, by concentrating and diafiltering the transferrin through an ultrafiltration membrane and/or sterile filtering the concentrated and/or diafiltering transferrin, as required.

Where a solution comprising haptoglobin and/or hemopexin and/or transferrin is to be used for clinical or veterinary applications (e.g., for administration to a subject with a condition associated with haemolysis), persons skilled in the art will understand that it may be desirable to reduce the level of active virus content (virus titre) and other potential infectious agents (for example prions) in the solution. This may be particularly desirable where the feedstock comprising haptoglobin and/or hemopexin and/or transferrin (i.e., the starting material) is derived from blood plasma. Methods of reducing the virus titre in a solution will be known to persons skilled in the art. Examples include pasteurization (for example, incubating the solution at 60° C. for 10 hours in the presence of high concentrations of stabilisers such as glycine (e.g. 2.75M) and sucrose (e.g. 50%) and/or other selected excipients or salts), dry heat treatment, virus filtration (passing the solution through a nano-filter; e.g., 20 nm cutoff) and/or subjecting the solution to treatment with a suitable organic solvent and detergent for a period of time and under conditions to inactivate virus in the solution. Solvent detergent has been used for over 20 years to inactivate enveloped viruses particularly in plasma-derived products. Thus it may be carried out using various reagents and methods known in the art (see, for example, U.S. Pat. No. 4,540,573 and U.S. Pat. No. 4,764,369 which are hereby incorporated by reference). Suitable solvents include tri-n-butyl phosphate (TnBP) and ether, preferably TnBP (typically at about 0.3%). Suitable detergents include polysorbate (Tween) 80, polysorbate (Tween) 20 and Triton X-100 (typically at about 0.3%). The selection of treatment conditions including solvent and detergent concentrations depend in part on the characteristics of the feedstock with less pure feedstocks generally requiring higher concentrations of reagents and more extreme reaction conditions. A preferred detergent is polysorbate 80 and a particularly preferred combination is polysorbate 80 and TnBP. The feedstock may be stirred with solvent and detergent reagents at a temperature and for a time sufficient to inactivate any enveloped viruses that may be present. For example, the solvent detergent treatment may be carried out for about 4 hours at 25° C. The solvent detergent chemicals are subsequently removed by for example adsorption on chromatographic media such as C-18 hydrophobic resins or eluting them in the drop-through fraction of ion exchange resins under conditions which adsorb the protein of interest.

The virus inactivation step can be performed at any suitable stage of the methods disclosed herein. In an embodiment, the feedstock comprising haptoglobin and/or hemopexin and/or transferrin is subject to a viral inactivation step prior to step (ii) from the first described aspect. In another embodiment, the solution comprising haptoglobin and/or hemopexin and/or transferrin that is recovered from the ammonium sulphate precipitation step (i.e., from steps (ii) and/or (iiii)) is subject to a viral inactivation step. In an embodiment disclosed herein, the viral inactivation step comprises pasteurisation or treatment with an organic solvent and detergent. In another embodiment disclosed herein, the virus inactivation step comprises virus filtration. Where virus filtration is used, the inventors have found that the addition of a free amino acid (e.g., arginine) prior to the filtration step can significantly improve the flux rate and recovery of haptoglobin and/or hemopexin and/or transferrin through the filter. An example of such method is described in U.S. Pat. No. 7,919,592.

In an embodiment disclosed herein, the feedstock or solution comprising haptoglobin and/or hemopexin and/or transferrin is subject to a viral inactivation step before it is passed through a chromatographic resin. The advantage of employing a virus inactivation step such as solvent detergent treatment prior to passing the treated solution or feedstock through a chromatographic resin such as an anion exchange resin is that it allows for the removal of the organic solvent and detergent from the treated solution by utilizing conditions that promote binding of the haptoglobin and/or hemopexin and/or transferrin to the resin and removal of the organic solvent and detergent with the flow-through (drop-through) fraction.

Pasteurization can generate protein aggregates and polymers. Therefore, it may be desirable in some instances to reduce the level of aggregates/polymers in a pasteurized solution. This can be achieved by any means knows to persons skilled in the art, although conveniently can be achieved by further chromatographic purification. In an embodiment disclosed herein, the pasteurized solution or feedstock is passed through an anion exchange chromatographic resin in positive mode with respect to the haptoglobin and/or hemopexin and/or transferrin such that any aggregates or polymers are removed with the flow-through (drop-through) fraction.

In another aspect of the present invention, there is provided a composition comprising the haptoglobin recovered by the methods disclosed herein. In an embodiment, the composition comprises a haptoglobin content of at least 80% of total protein. In another embodiment, the composition comprises a haptoglobin content of at least 90% of total protein. In another embodiment, the composition comprises a haptoglobin content of at least 95%. In yet another embodiment, the composition comprises a haptoglobin content of at least 98%.

In another aspect of the present invention, there is provided a composition comprising the hemopexin recovered by the methods disclosed herein. In an embodiment, the composition comprises a hemopexin content of at least 80% of total protein. In another embodiment, the composition comprises a hemopexin content of at least 90% of total protein. In another embodiment, the composition comprises a hemopexin content of at least 95%. In another embodiment, the composition comprises a hemopexin content of at least 97%. In yet another embodiment, the composition comprises a hemopexin content of at least 98%.

In another aspect of the present invention, there is provided a composition comprising the transferrin recovered by the methods disclosed herein. In an embodiment, the composition comprises a transferrin content of at least 80% of total protein. In another embodiment, the composition comprises a transferrin content of at least 90% of total protein. In another embodiment, the composition comprises a transferrin content of at least 95%. In yet another embodiment, the composition comprises a transferrin content of at least 98%.

In another aspect of the present invention, there is provided a composition comprising the haptoglobin recovered by the methods disclosed herein and the hemopexin recovered by the methods disclosed herein. In an embodiment, the composition comprises a combined haptoglobin and hemopexin content of at least 80% of total protein. In another embodiment, the composition comprises a combined haptoglobin and hemopexin content of at least 90% of total protein. In another embodiment, the composition comprises a combined haptoglobin and hemopexin content of at least 95% of total protein. In yet another embodiment, the composition comprises a combined haptoglobin and hemopexin content of at least 98% of total protein.

In an embodiment, the composition further comprises the transferrin recovered by the methods disclosed herein. In an embodiment, the composition comprises a combined haptoglobin, hemopexin and transferrin content of at least 80% of total protein. In another embodiment, the composition comprises a combined haptoglobin, hemopexin and transferrin content of at least 90% of total protein. In another embodiment, the composition comprises a combined haptoglobin, hemopexin and transferring content of at least 95% of total protein. In yet another embodiment, the composition comprises a combined haptoglobin, hemopexin and transferrin content of at least 98% of total protein.

In another aspect of the present invention, there is provided a composition comprising a haptoglobin content of at least 80%, 90%, 95%, or 98% of total protein. In another aspect of the present invention, there is provided a composition comprising a hemopexin content of at least 80%, 90%, 95%, or 98% of total protein. In another aspect of the present invention, there is provided a composition comprising a combined hemopexin and haptoglobin content of at least 80, 90%, 95%, or 98% of total protein. In yet another aspect of the present invention, there is provided a composition comprising a combined hemopexin, haptoglobin and transferrin content of at least 80, 90%, 95%, or 98% of total protein.

The compositions comprising haptoglobin, hemopexin and/or transferrin recovered by the methods of the present invention disclosed herein will be substantially free of other components with which they are normally associated (e.g., other plasma-derived proteins). Thus, in an embodiment, the composition comprising haptoglobin, hemopexin and/or transferrin will comprise less than 20% of total protein, preferably less than 10% of total protein, and more preferably less than 5% of total protein of other components with which they are normally associated (i.e., impurities). The skilled person will understand that the level of impurities present in the compositions of the present invention may depend on the intended use of the compositions. For example, where the compositions are to be administered to a human subject in need thereof (i.e., for clinical use), it would be desirable that the composition comprises less than 5% impurities (of total protein). Conversely, where the proteins are to be used in vitro, it may be acceptable if the composition comprises more than 5% of impurities (of total protein).

In another aspect of the present invention, there is provided a formulation comprising the composition of the present invention, as disclosed herein, and a pharmaceutically acceptable carrier.

Suitable pharmaceutically acceptable carriers, diluents and/or excipients are known to those skilled in the art. Examples include solvents, dispersion media, antifungal and antibacterial agents, surfactants, isotonic and absorption agents and the like.

The pharmaceutical formulation may also be formulated by the addition of (or a combination of) suitable stabilisers, for example, an amino acid, a carbohydrate, a salt, and a detergent. In particular embodiments, the stabiliser comprises a mixture of a sugar alcohol and an amino acid. The stabilizer may comprise a mixture of a sugar (e.g. sucrose or trehalose), a sugar alcohol (e.g. mannitol or sorbitol), and an amino acid (e.g. proline, glycine and arginine). In a preferred embodiment, the formulation comprises an amino acid such as arginine. In other embodiments, the formulation comprises divalent metal ions in a concentration up to 100 mM and a complexing agent as described in U.S. Pat. No. 7,045,601. In embodiments where the pH is preferably about 6.5 to 7.5 and the osmolality is at least 240 mosmol/kg.

The pharmaceutical formulation may also be sterilised by filtration prior to dispensing and long term storage. Preferably, the formulation will retain substantially its original stability characteristics for at least 2, 4, 6, 8, 10, 12, 18, 24, 36 or more months. For example, formulations stored at 2-8° C. or 25° C. can typically retain substantially the same molecular size distribution as measured by HPLC-SEC when stored for 6 months or longer. Particular embodiments of the pharmaceutical formulation can be stable and suitable for commercial pharmaceutical use for at least 6 months, 12 months, 18 months, 24 months, 36 months or even longer when stored at 2-8° C. and/or room temperature.

The compositions described herein may be formulated into any of many possible dosage forms such as injectable formulations. The formulations and their subsequent administration (dosing) are within the skill of those in the art. Dosing is dependent on the responsiveness of the subject to treatment, but will invariably last for as long as the desirable effect (e.g., a reduction in the level of free Hb/heme) is desired. Persons of ordinary skill can easily determine optimum dosages, dosing methodologies and repetition rates.

In an embodiment disclosed herein, the pharmaceutical formulation of the present invention is a solution that has a volume of at least 5 mL and comprises at least 5 mg/mL haptoglobin and/or hemopexin and/or transferrin. In another embodiment, the pharmaceutical formulation has a volume of at least 5 mL and comprises at least 20 mg/mL haptoglobin and/or hemopexin and/or transferrin. In particular embodiments, the pharmaceutical formulation has a volume of at least 5 mL and comprises haptoglobin and/or hemopexin and/or transferrin at a concentration of about 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 90 mg/mL, 100 mg/mL, 150 mg/mL or 200 mg/mL. In another aspect, there is provided a vessel containing at least 5 mL of a stable pharmaceutically acceptable haptoglobin and/or hemopexin and/or transferrin solution, wherein the concentration of haptoglobin and/or hemopexin and/or transferrin is at least 20 mg/mL.

In another aspect of the present invention, there is provided a method of treating a condition associated with haemolysis, the method comprising administering to a subject in need thereof the composition or the formulation of the present invention, as disclosed herein.

The term "subject", as used herein, refers to an animal which includes a primate (a lower or higher primate). A higher primate includes human. Whilst the present invention has particular application to targeting conditions in humans, it would be understood by those skilled in the art that non-human animals may also benefit from the compositions and methods disclosed herein. Thus, it will be appreciated by the skilled addressee that the present invention has both human and veterinary applications. For convenience, an "animal" includes livestock and companion animals such as cattle, horses, sheep, pigs, camelids, goats, donkeys, dogs and cats. With respect to horses, these include horses used in the racing industry as well as those used recreationally or in the livestock industry.

The compositions or formulations of the present invention may be administered to the subject a number of ways. Examples of suitable routes of administration include intravenous, subcutaneous, intra-arterial or by infusion. In an embodiment, the molecules are administered intravenously.

Where necessary, the methods of the present invention may further comprise administering a second therapeutic agent. The second therapeutic compound may be co-administered to the subject sequentially (before or after administration of the compositions or formulations disclosed herein) or concurrently. In an embodiment, the second therapeutic agent is an iron chelating agent (e.g., deferrioxamine or deferiprone).

In another aspect of the present invention, there is provided use of the compositions or formulations of the present invention, as disclosed herein, in the manufacture of a medicament for treating a condition associated with haemolysis. Such compositions or formulations are preferably suitable for use in human patients.

Conditions associated with haemolysis and which are at risk of haemoglobin/heme-mediated toxicity, are known in the art. In an embodiment, the condition is selected from an acute haemolytic condition and/or a chronic haemolytic condition. In an embodiment, the condition is selected from the group consisting of haemolytic anaemia, transfusion-induced haemolysis, haemolytic uraemic syndrome, an autoimmune disease, malaria infection, trauma, blood transfusion, open heart surgery using cardiopulmonary bypass and burns, including in the treatment of hemoglobinemia or hemoglobinuria accompanied with hemolysis after burn. In an embodiment, the condition is selected from the group consisting of sickle cell anaemia, hereditary spherocytosis, hereditary elliptocytosis, thalassemia, congenital dyserythropoietic anemia and Paroxysmal nocturnal hemoglobinuria, systemic lupus erythematosus and chronic lymphocytic leukemia.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Example 1

Starting Material: Cohn Fraction IV4 Precipitate was used as starting material for the purification of haptoglobin, hemopexin, and transferrin (see FIG. 1).

Precipitate Extraction: Extraction of the precipitate was performed by the introduction of 20 grams of Extraction Buffer per gram of Fraction IV4 Precipitate (20× Extraction Ratio). The buffer and the precipitate were mixed for a minimum of 1 hour. Extraction Buffer consisted of 50 mM Tris adjusted to a pH of 7.0 with Concentrated HCl. The Extraction Buffer was prepared at a temperature of 20-25° C. The precipitate extraction was also performed at a temperature of 20-25° C. The pH during the extraction was maintained between 7.0 to 8.0 (preferably 7.0) for the duration of the 1 hour extraction time.

Ammonium Sulfate Precipitation: Solid ammonium sulfate was added to the Fraction IV4 extract in order to achieve a final concentration of 2.0 to 2.5M (preferably 2.4M). Under agitation, the ammonium sulfate was slowly added to the extract and allowed to continually mix for a minimum of 1 hour. The ammonium sulfate precipitation was performed at a temperature of 20-25° C.

Figure 2:
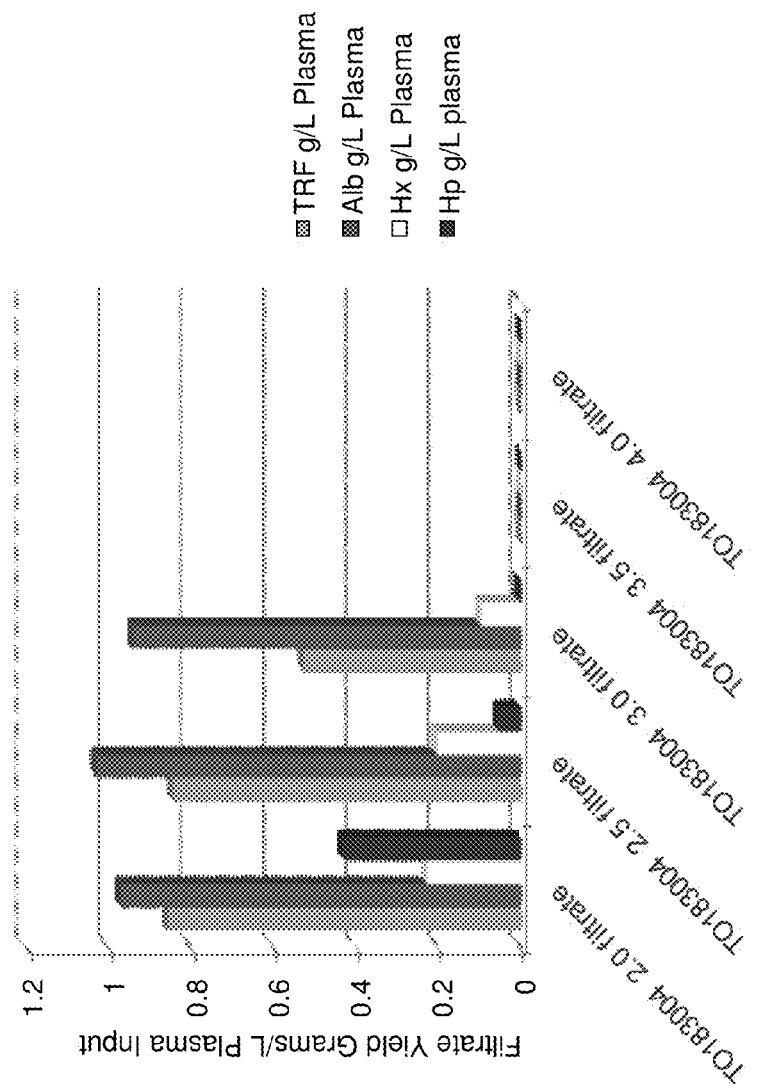
FIG. 2 shows the recovery of transferrin (TRF), Albumin (Alb), hemopexin (HPX) and haptoglobin (HAP) in the remaining filtrate following precipitation in the presence of 2.0M, 2.5M, 3.0M, 3.5M and 4.0M ammonium sulfate.

An ammonium sulfate concentration of 2.5M was utilized to precipitate lipids, and clarify the Fraction IV4 Extract, while keeping hemopexin and transferrin soluble. Coincidentally, this ammonium sulfate concentration resulted in the precipitation of a significant portion of the haptoglobin present in the Fraction IV4 Extract (see FIG. 2). The precipitation of haptoglobin at 2.2M to 2.5M ammonium sulfate, while hemopexin remained soluble, allows for the co-purification of hemopexin and haptoglobin from the same starting fraction.

Figure 3:
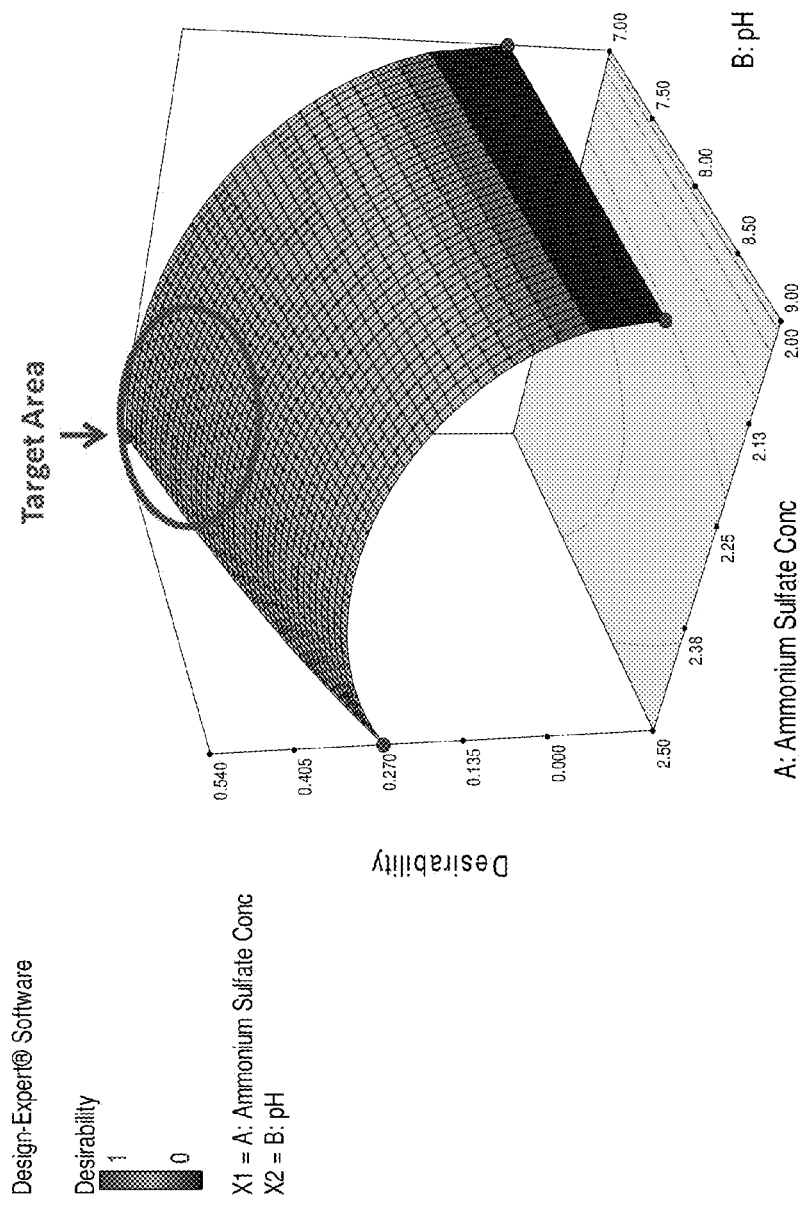
FIG. 3 shows a desirability plot of the design of experiment (DOE), showing the desirable conditions that would precipitate the haptoglobin from the plasma fraction, while keeping the hemopexin in solution. A DOE is a set of controlled experimentation that was used to evaluate the impact of pH and ammonium sulfate concentration on the ability to separate hemopexin from haptoglobin. A factorial mathematical design was used to design and analyze the data. The desirability plot depicted in FIG. 3 uses this mathematical design to determine the most desirable conditions that would result in the best separation and recovery of both hemopexin and haptoglobin.

To further narrow the acceptable ammonium sulfate concentration range, a design of experiment (DOE) was performed which looked at the impact of pH and ammonium sulfate concentration. FIG. 3 shows the desirability plot of the DOE. This plot gives the most desirable conditions that would precipitate the most haptoglobin while keeping the most hemopexin soluble. The desirability plot shows that a pH maintained between 7-8 (preferably 7.0) and an ammonium sulfate concentration between 2.2M and 2.5M (preferable 2.4M) is optimal for separating both proteins from the same staring material. Moreover, transferrin remains soluble at concentrations greater than 2.5M, hence, these conditions were optimal for the purification of all three proteins from the same starting material.

Filtration: To prepare the ammonium sulfate treated extract for filtration, 10 grams of C1000 filter aid was added per liter of plasma equivalent utilized for the batch. The C1000 filter aid was allowed to mix for a minimum of 15 minutes prior to the execution of filtration. A plate and frame filter press was utilized for the filtration to allow for collection of the haptoglobin-enriched precipitate. The plate and frame filter press was assembled with a sheet of type 175 filter paper in front of a 3M (Cuno) 70CA depth filtration filter sheet. For every 3 L of plasma equivalent input into the batch, 0.193 mL of precipitate collection area was required (3 L Plasma/4" Ertel 4S Filter Frame). The ammonium sulfate treated extract was then pumped into the filter press through the use of a double diagram pressurized air actuated pump.

After the completion of the C1000 mix time, the treated extract was pumped into the filter press and the filtrate was collected after a single pass through the filter press. The filter press was then post-washed with 1 to 2 press volumes of 2.4M ammonium sulfate, 50 mM Tris, adjusted to pH 7.0. The filtration process was performed at a temperature of 20-25° C. The resulting filtrate contains hemopexin and can be stored at 2-8° C. until it is carried forward for further purification. The resulting precipitate contains haptoglobin and can be stored at less than or equal to −20° C. until it is carried forward for further purification.

Figure 8:
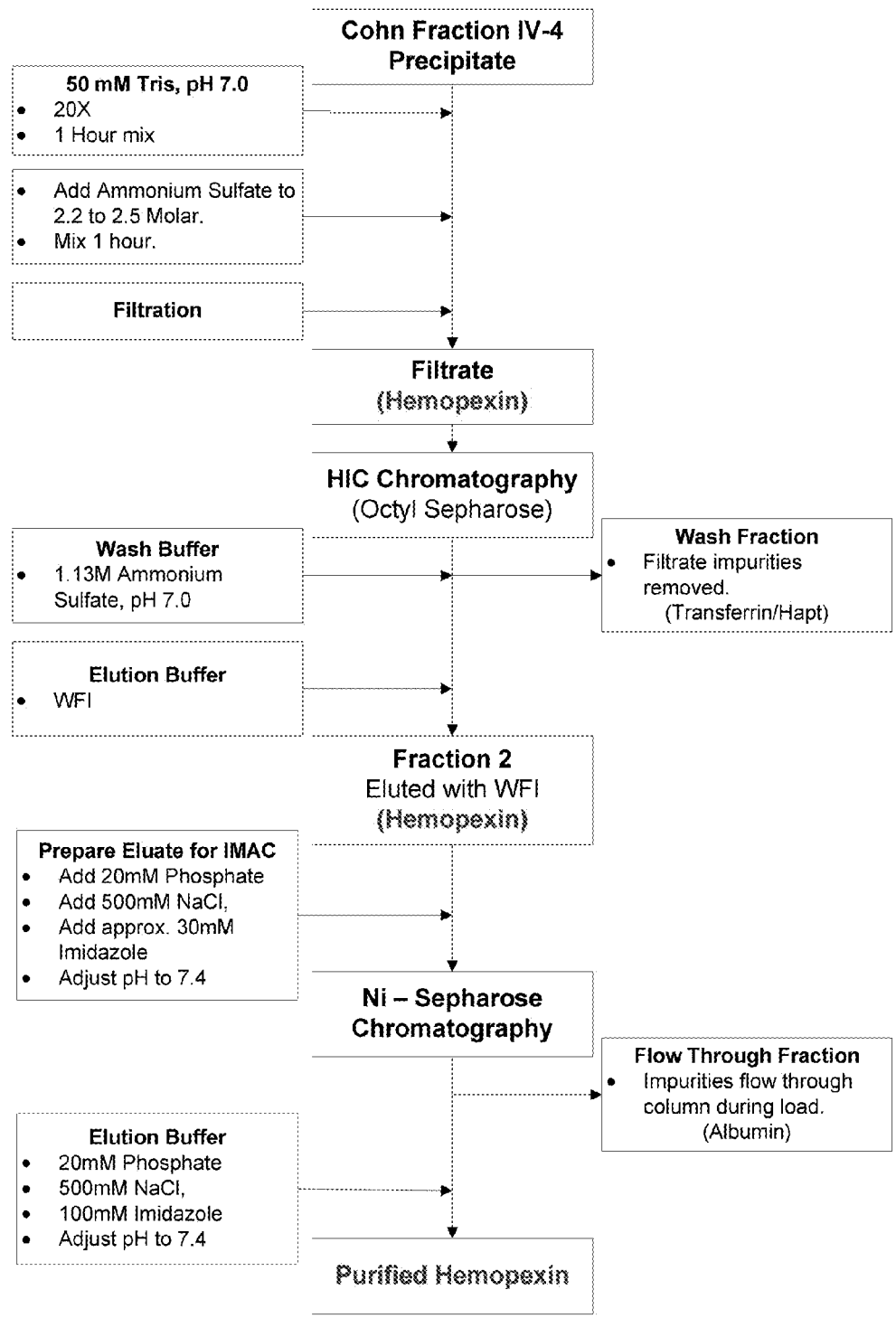
FIG. 8 is a flow diagram of a hemopexin purification process in accordance with an embodiment disclosed herein.

Purification of Hemopexin (Hx) from the Filtrate Fraction:

The Hx process scheme is highlighted in FIG. 8.

(a) Octyl Sepharose Chromatography (HIC): The filtrate obtained from the extraction and ammonium sulfate treatment of Fraction IV4 precipitate was further clarified using a 0.22 μm filter. The filtrate was then loaded onto an Octyl Sepharose column (GE Lifesciences) that had been equilibrated with three column volumes of 2.5M ammonium sulfate, 50 mM Tris, at pH 7.4. Eight to 12 column volumes (Target=10) of filtrate were loaded onto the Octyl Sepharose column Impurities and any unbound protein were washed off of the column with 3 column volumes of 0.9M to 1.2M (Target 1.13M) ammonium sulfate, 50 mM Tris, at pH 7.4 (Wash). The wash fraction contained transferrin, which can be saved for further purification. The hemopexin containing fraction (Eluate) was then eluted off of the column with three column volumes of water (WFI). The Eluate was then stored at 2-8° C. until used for further purification. The Octyl Sepharose (HIC) purification was performed at a temperature of 20-25° C.

Figure 4:
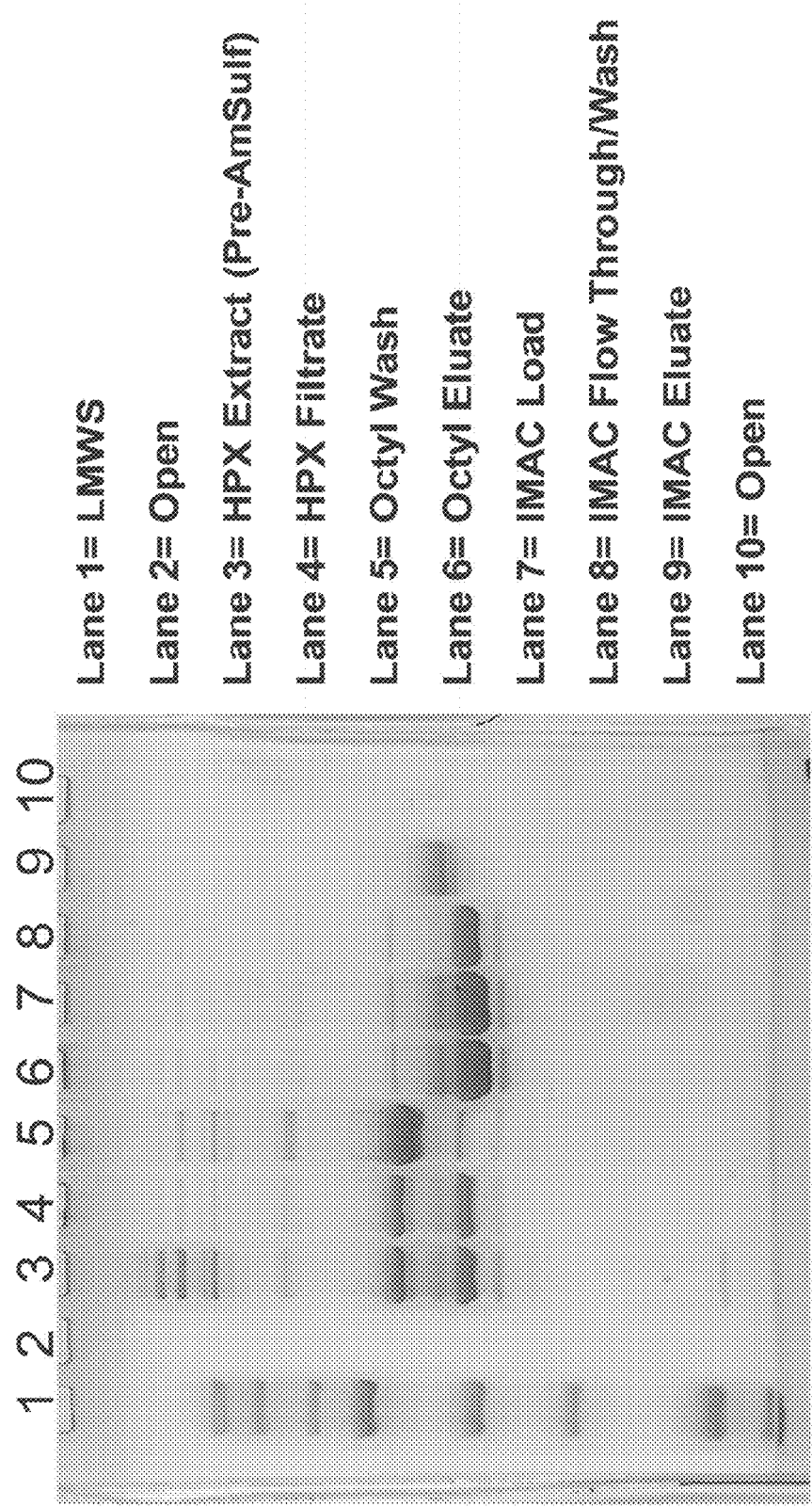
FIG. 4 shows SDS-PAGE electrophoresis of hemopexin recovered following the various steps in the purification process disclosed herein. SDS-PAGE analysis was performed using pre-cast 10% Tris-Glycine gels. All samples were diluted to a concentration of 0.1 mg/mL in Tris-Glycine SDS sample buffer and 20 uL of each sample was loaded into the sample well of the gel. Run time and Voltage were set to the gel manufacturer's recommendations. Each gel was stained with an easy to use type of Coomassie Brilliant Blue stain solution purchased direct from a manufacturer.

(b) Ni-Sepharose Chromatography (IMAC): 20 mM sodium phosphate, 500 mM sodium chloride, and 30 mM imidazole were added to the Octyl Sepharose Eluate. Once added, the pH of the Octyl Sepharose Eluate was adjusted to 7.4. Two to 3 column volumes of the Octyl Sepharose Eluate were then loaded onto a Ni-Sepharose (GE Lifesciences) column that had been equilibrated with buffer containing 20 mM sodium phosphate, 500 mM sodium chloride and optionally 30 mM imidazole, adjusted to pH 7.4. The addition of imidazole to the Octyl Sepharose Eluate (load) reduces the affinity of the Ni-Sepharose to albumin and other impurities, while maintaining its binding affinity to hemopexin. Therefore, during the load step, the impurities flowed through the column, while the hemopexin bound to the resin. After the completion of the load, the column was washed with 2 column volumes of 20 mM sodium phosphate, 500 mM sodium chloride and 30 mM imidazole, pH 7.4 to remove any unbound impurities. The hemopexin was then eluted from the column using 20 mM sodium phosphate, 500 mM sodium chloride and 100 mM imidazole, at pH 7.4. The hemopexin present in the Ni-Sepharose eluate was estimated to be greater than 95% by SDS-PAGE (see FIG. 4). The Ni-Sepharose chromatography (IMAC) process was performed at 20-25° C. and the resulting eluate was stored at less then or equal to −20° C. until use.

(c) Concentration/Diafiltration: The Ni-Sepharose Eluate was concentrated to a desired concentration (1-20% w/v), then diafiltered with 10 volumes of phosphate buffered saline per volume of concentrate. The concentration and diafiltration were performed using a 30 kD ultrafiltration membrane. Once the diafiltration was completed and the concentrate was at the desired concentration, the hemopexin was optionally formulated with a sugar and or amino acid, sterile filtered and stored at less than or equal to −20° C. The purified hemopexin can be in pre-clinical animal and cellular studies in this form.

The final yield of hemopexin recovered from the process was estimated to be approximately 0.151 g/L plasma.

The concentrated hemopexin preparation (approximately 2.3% w/v) was characterised by immune-nephelometry. Plasma proteins such as IgG, IgA, IgM, alpha-1-antitrypsin, transferrin, alpha-1-acid glycoprotein, pre-albumin, ceruloplasmin, apolipoprotein A-I, apolipoprotein B and anti-thrombin III were below detectable levels. Only trace amounts were detected for other plasma proteins, such as haptoglobulin (0.165 mg/mL) and albumin (0.038 mg/mL). These results indicate that Hx accounted for at least 99% of the total protein in the preparation.

A further batch of hemopexin was processed according to the methods described above. The batch was concentrated to 35 mg/mL protein. Analysis of the batch indicated a hemopexin purity of about 98% with the impurities including 1.6% haptoglobin, 0.3% transferrin, 0.2% albumin, and 0.1% alpha-2 macroglobulin.

Purification of Haptoglobin (Hp) from the 2.5M Ammonium Sulfate Precipitate

Figure 9:
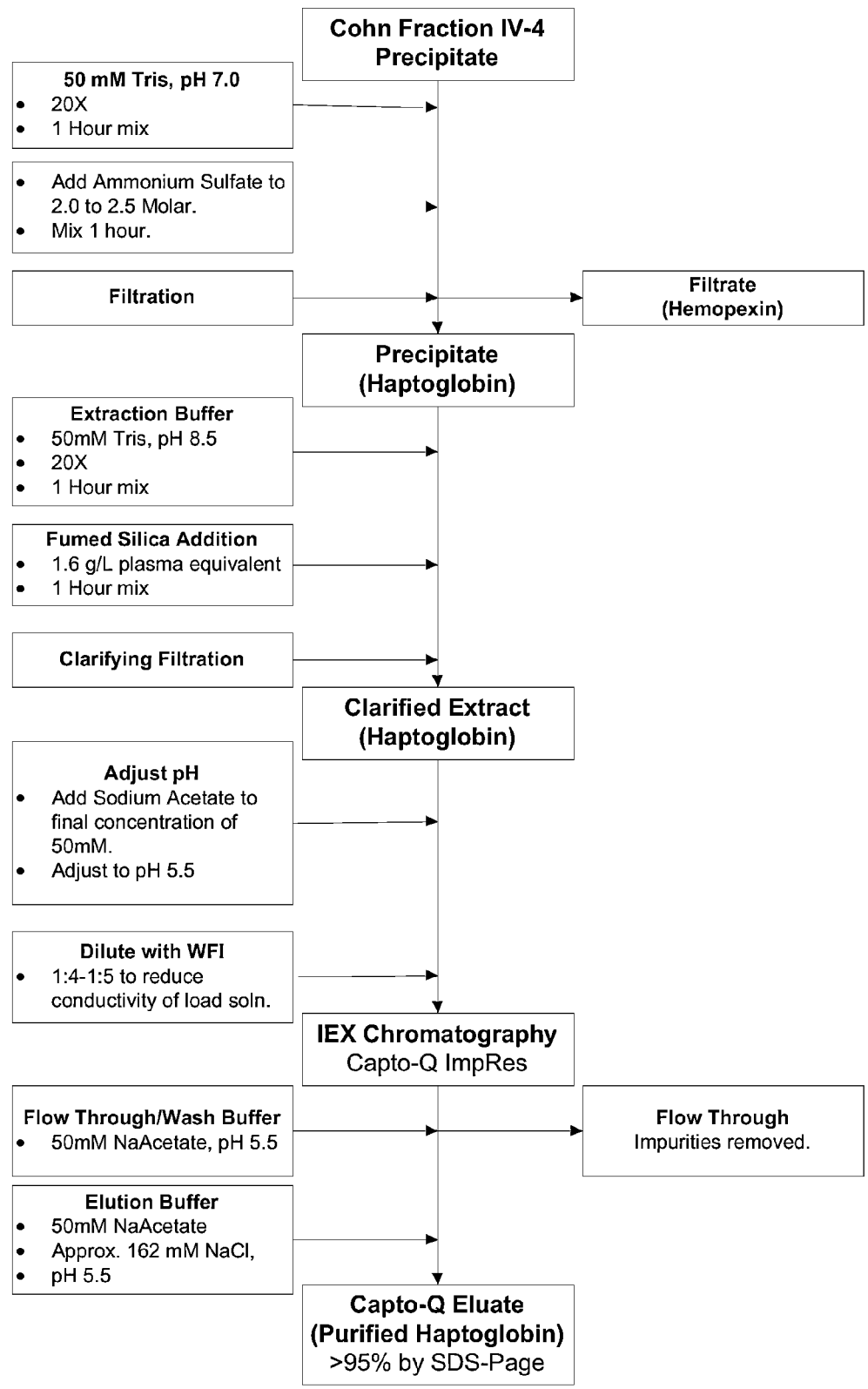
FIG. 9 is a flow diagram of a haptoglobin purification process in accordance with an embodiment disclosed herein.

The Hp process scheme is highlighted in FIG. 9.

(a) Precipitate Extraction and Filtration: Haptoglobin was extracted from the precipitate by the introduction of 20 grams of extraction buffer/gram of precipitate (20× ratio). The extraction buffer consisted of 50 mM Sodium Acetate, adjusted to pH 5.5. The buffer and the precipitate were mixed for a minimum of 1 hour. After 15 minutes, the pH was adjusted to within the range of 5.4 to 5.6. The low pH extraction buffer was utilized to reduce lipid extraction while the low pH was utilized during the subsequent chromatography step. To remove remaining filter aid and undissolved protein and lipids, the extract was then passed through a Cuno 70CA filter or equivalent depth filter. The filtrate was then clarified by use of a 0.2 μm filter. The resulting filtrate was ready for the subsequent chromatography step. The extraction buffer preparation, the extraction process, and the filtration process were all performed at 20-25° C.

In another embodiment the Haptoglobin was extracted from the precipitate by the introduction of 20 grams of extraction buffer/gram of precipitate (20× ratio). The extraction buffer consisted of 50 mM Tris, adjusted to pH 8.5. The buffer and the precipitate were mixed for a minimum of 1 hour. After 15 minutes, the pH was adjusted to within the range of 8.4 to 8.6. To reduce the lipid content and aid in clarification of the extracted precipitate a lipid adsorption agent, Aerosil (fumed silica), was added at 1.6 grams per liter of plasma equivalent. The Aerosil treated extract was then allowed to mix for a minimum of 1 hour. To remove remaining filter aid and any undissolved protein and lipids, the extract was passed through a Cuno 70CA filter or other similar depth filter. The filtrate was then clarified by use of a 0.2 μm filter. The resulting filtrate was ready for the subsequent chromatography step. The extraction buffer preparation, the extraction process, and the filtration process were all performed at 20-25° C.

Figure 5:
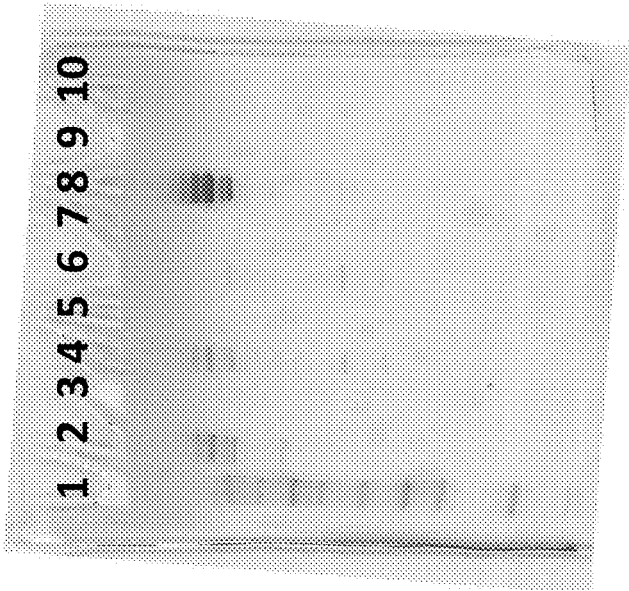
FIG. 5 shows an SDS-PAGE electrophoresis (using the method described above in FIG. 4) of haptoglobin intermediates recovered following the various steps in the purification process disclosed herein.
Figure 6:
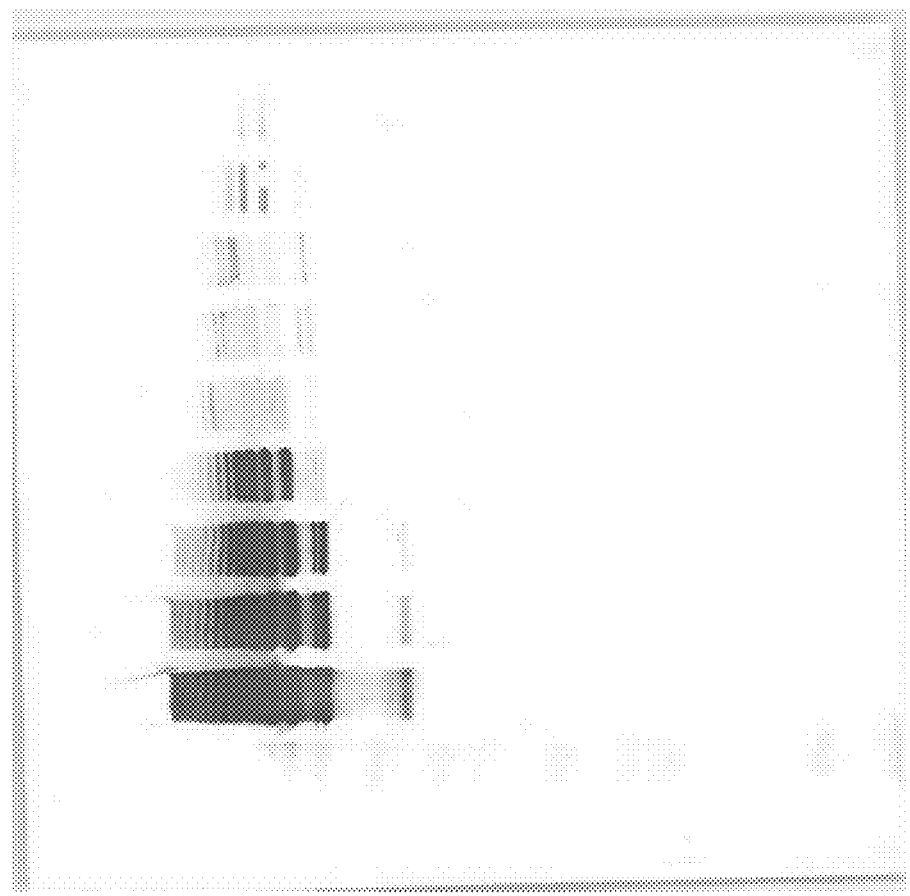
FIG. 6 shows a Western Blot of the Capto Q Eluate on a 10% Tris-Glycine Non-Reduced SDS-PAGE electrophoresis gel (using the method described in FIG. 4). The separated proteins are then transferred to a nitrocellulose membrane and the membrane is blocked to prevent any non-specific binding of antibody. The nitrocellulose membrane is then incubated with a solution containing antibodies to Human Haptoglobin. A secondary antibody linked to horseradish peroxidase is then incubated with the nitrocellulose membrane. The nitrocellulose is then developed with a solution containing peroxide thereby only visualizing the protein bands that specifically contain Human Haptoglobin. All lanes contain Capto Q ImpRes Eluate at different concentrations. The Western blot indicates that most of the bands present in the Capto Q Eluate are haptoglobin.

(b) Capto Q ImpRes Chromatography Step: Sodium acetate was added to the filtrate obtained from the above step, to a final concentration of 50 mM, and the pH of the filtrate is adjusted to pH 5.5. The pH adjusted filtrate was then diluted 1:4 to 1:5 with water (WFI) and loaded onto a GE Healthcare Capto Q ImpRes chromatography column that was equilibrated with 50 mM sodium acetate, pH 5.5. The load requires sodium acetate as a low pH buffer and dilution with water is required in order to reduce the conductivity of the load so that haptoglobin can bind to the column After completion of the load, the column was washed with 2 column volumes of 50 mM sodium acetate, pH 5.5 to remove any unbound contaminate proteins. The haptoglobin was then eluted with 4 column volumes of 50 mM sodium acetate, 100-200 mM NaCl (preferably 162 mM), pH 5.5. A wide NaCl concentration range of the elution buffer is required as the elution conditions are partially dependant on the load volume utilized. The eluate can be stored at 2-8° C., short term, and at less than or equal to −20° C., long term, until concentration/diafiltration. The haptoglobin content of the Capto Q ImpRes eluate was estimated to be greater than 95% by SDS-PAGE (see FIGS. 5 and 6). The chromatography buffers and chromatography steps were all performed at 20-25° C.

(c) Concentration/Diafiltration: The Capto Q ImpRes Eluate was concentrated to a specified concentration, then diafiltered with 10 volumes of phosphate buffered saline per volume of concentrate. The concentration and diafiltration were performed using a 30 kD ultrafiltration membrane. Once the diafiltration was completed and the concentrate was at the desired concentration, the purified haptoglobin solution was sterile filtered and stored at less than or equal to −20° C.

Optionally, a lipid adsorption step can be conducted before or after the anion exchange chromatography step or after the concentration/diafiltration step. An example of a suitable lipid adsorption agent is a fumed silica like Aerosil (e.g. Aerosil 380).

The final yield of haptoglobin recovered from the process was estimated to be approximately 0.285 g/L plasma input.

The concentrated haptoglobin preparation (approximately 2.6% w/v) was characterised by immune-nephelometry. Plasma proteins such as IgG, IgM, alpha-1-acid glycoprotein, pre-albumin, ceruloplasmin, hemopexin, apolipoprotein A-I, apolipoprotein B and antithrombin III were below detectable levels, whilst only trace amounts were detected for other plasma proteins such as transferrin (0.099 mg/mL), alpha-1-antitrypsin (0.062 mg/mL), alpha-2-macroglobulin (0.086 mg/mL), IgA (0.65 mg/mL), and albumin (0.123 mg/mL). These results indicate that Hp accounted for at least 96% of the total protein in the preparation.

Purification of Transferrin from the Octyl 1.13M Ammonium Sulfate Wash Fraction:

Prior to performing ion-exchange chromatography on the Octyl Wash Fraction, the ammonium sulfate was diafiltered out and exchanged with a lower ionic strength buffer. To this end, the Octyl Eluate was concentrated and diafiltered against 10 volumes of 50 mM Tris, pH 7.0 per volume of eluate. The concentration and diafiltration were performed using a 30 kD ultrafiltration membrane.

Figure 7:
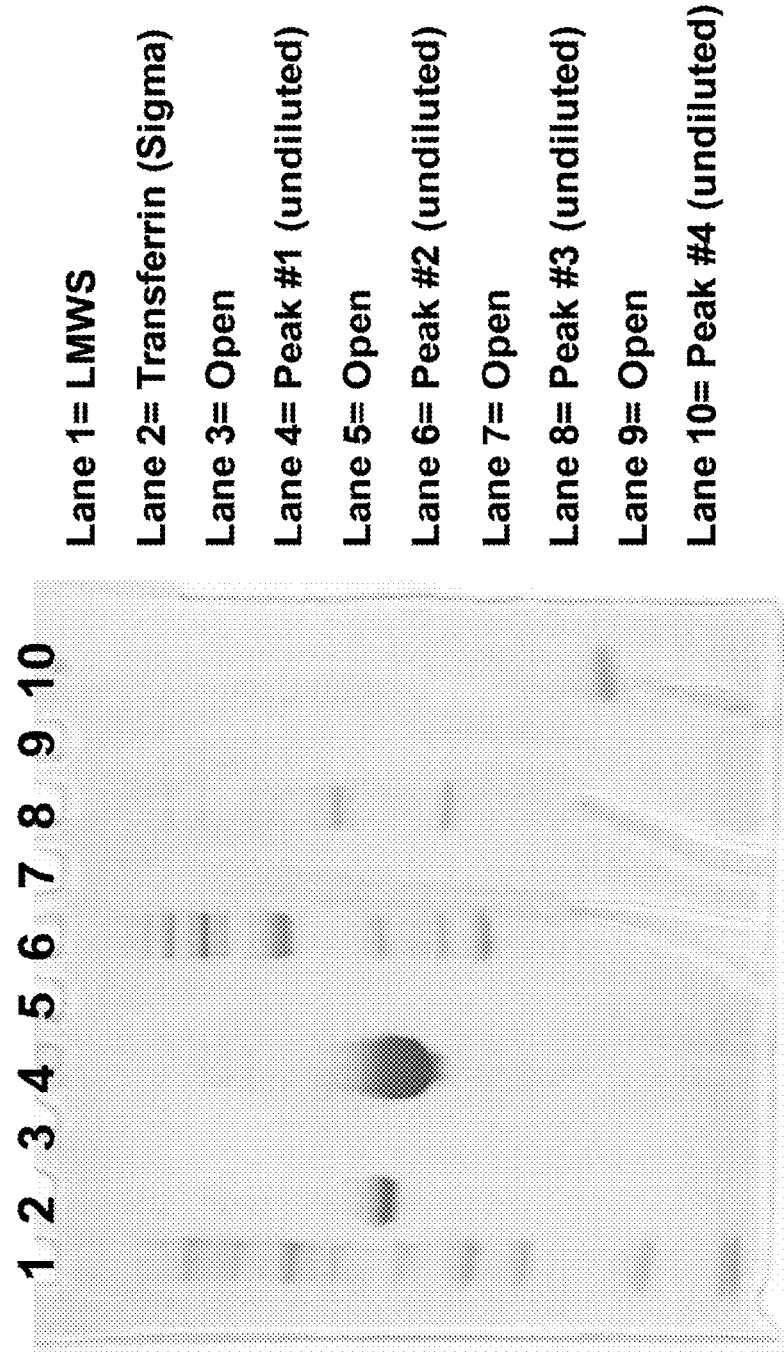
FIG. 7 shows SDS-PAGE electrophoresis of transferrin recovered from ion-exchange chromatography (Capto DEAE) following the various steps in the purification process disclosed herein. Peak one is heavily loaded, but appears to be pure transferrin. This indicates that it is possible to purify transferrin from the Octyl Sepharose Wash fraction, which also means that it is possible to purify hemopexin, haptoglobin, and transferrin from the same starting material.
Figure 10:
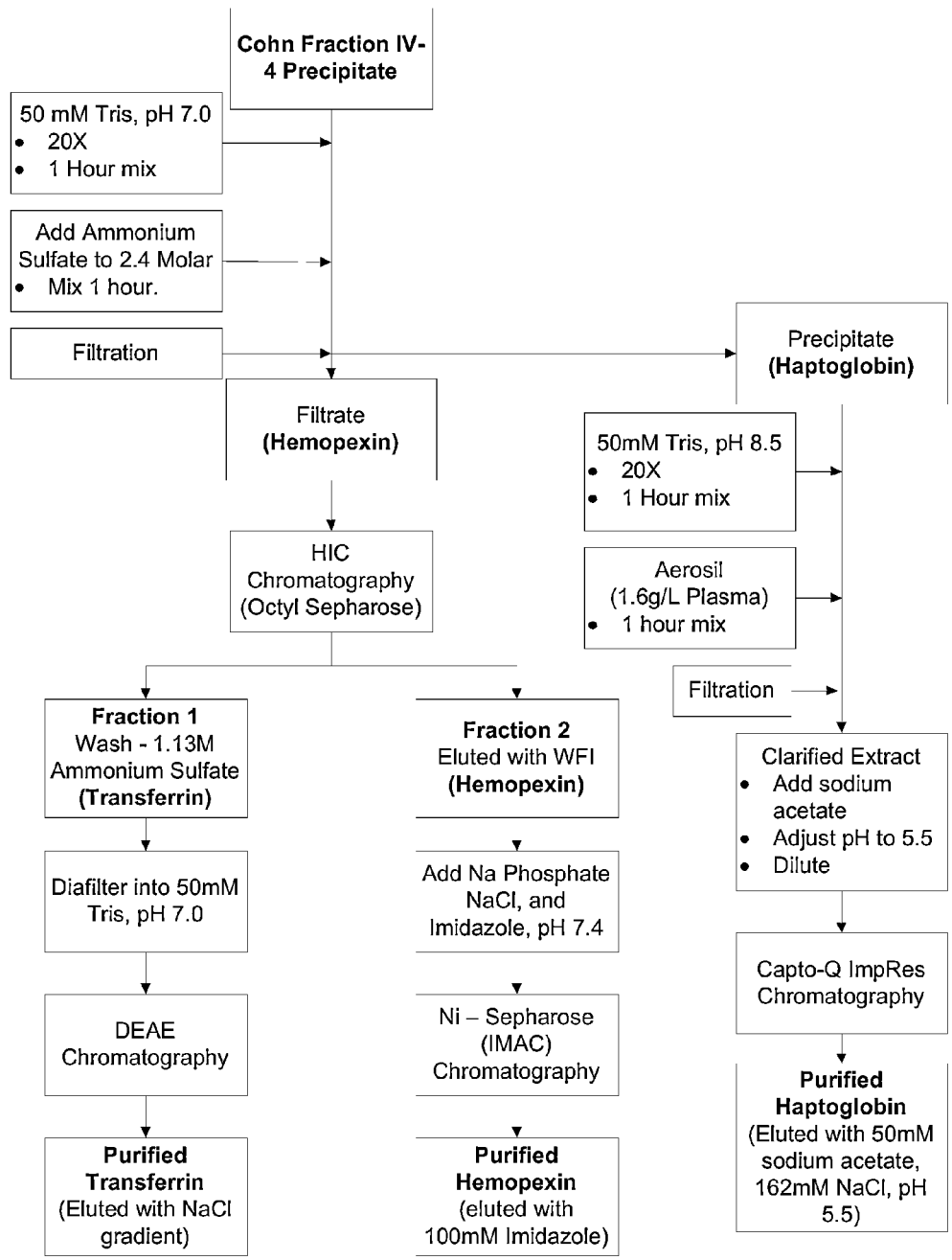
FIG. 10 is a flow diagram of a combined haptoglobin/hemopexin/transferrin purification process in accordance with an embodiment disclosed herein.

The diafiltered wash fraction was then loaded onto a GE Healthcare Capto DEAE column equilibrated with 50 mM Tris, pH 7.0. To determine if it was feasible to obtain pure transferrin from this fraction, a linear gradient was performed over 10 column volumes using 50 mM Tris, pH 7.0 as the starting buffer and ending with 50 mM Tris, 0.5M NaCl, pH 7.0. Fractions were collected that correspond to each peak on the chromatogram. SDS-PAGE analysis was performed to determine if one of the peaks contained pure transferrin. As seen in FIG. 7, peak one was heavily loaded, but appeared to be pure transferrin. This indicates that it is possible to purify transferrin from the Octyl Sepharose Wash fraction, which also means that it is possible to purify hemopexin, haptoglobin, and transferrin from the same starting material (see also FIG. 10).

The invention claimed is:

1. A method of purifying haptoglobin and hemopexin from a solution containing both proteins, the method comprising:
   (i) providing a solution containing both haptoglobin and hemopexin;
   (ii) precipitating the haptoglobin from the solution by adding ammonium sulfate to the solution;
   (iii) separating the precipitated haptoglobin from the solution containing hemopexin; and
   (iv) separately purifying the haptoglobin and/or hemopexin in one or more steps,
wherein the haptoglobin is precipitated from the solution, at a pH of 6 to 8, by adding 2.3 M to 2.5 M ammonium sulfate to the solution.

2. The method of claim 1, wherein the haptoglobin is precipitated from the solution by adding about 2.4M ammonium sulfate to the solution.

3. The method of claim 1, wherein the haptoglobin is precipitated from the solution at a pH of about 7.

4. The method of claim 1, wherein the solution containing both haptoglobin and hemopexin further comprises transferrin.

5. The method of claim 1, wherein the solution is a human plasma fraction.

6. The method of claim 5, wherein the solution is a Cohn Fraction IV.

7. The method of claim 6, wherein the solution is a Cohn Fraction $IV_4$.

8. The method of claim 1, wherein the method further comprises:
   (i) dissolving the precipitated haptoglobin in a buffer to obtain a haptoglobin solution;
   (ii) passing the haptoglobin solution through a strong anion exchange chromatographic resin under conditions such that the haptoglobin binds to the resin;
   (iii) eluting the haptoglobin from the resin; and
   (iv) recovering the eluted haptoglobin.

9. The method of claim 8, further comprising exposing the haptoglobin solution to a lipid removal agent under conditions that allow lipid to bind to the agent.

10. The method of claim 1, wherein the method further comprises:
    (a) passing the solution containing hemopexin through a hydrophobic interaction chromatographic resin under conditions that allow the hemopexin to bind to the resin;
    (b) collecting the flow-through fraction from step (a);
    (c) optionally washing the resin following step (b) and collecting the flow-through wash fraction; and
    (d) eluting the hemopexin from the resin following step (b) and/or following step (c); and
    (e) recovering the eluted hemopexin.

11. The method of claim 10, further comprising:
    (i) passing the eluted hemopexin through a metal ion affinity chromatographic resin under conditions that allow the hemopexin to bind to the resin;
    (ii) eluting the hemopexin from the resin; and
    (iii) recovering the eluted hemopexin.

12. The method of claim 4, further comprising:
    (a) passing the solution containing hemopexin through a hydrophobic interaction chromatographic resin under conditions that allow the hemopexin to bind to the resin;
    (b) collecting the flow-through fraction from step (a);
    (c) optionally washing the resin following step (b) and collecting the flow-through wash fraction;
    (d) passing the flow-through fraction from step (b) and/or the flow-through wash fraction from step (c) through a weak anion exchange chromatographic resin under conditions such that transferrin binds to the resin; and
    (e) recovering the transferrin from the resin.

* * * * *